(12) United States Patent
Das et al.

(10) Patent No.: US 8,217,188 B2
(45) Date of Patent: Jul. 10, 2012

(54) 2H-CHROMENES ANNELATED AT $C_5$-$C_6$ AND METHODS OF MAKING AND USING THEREOF

(75) Inventors: Suresh Das, Kerala (IN); Bruno Dufour, Champagne sur Seine (FR); Mangalam S Nair, Kerala (IN); Kokkuvayil V Radhakrishnan, Kerala (IN)

(73) Assignee: Corning Incorporated, Corning, NY (US)

( * ) Notice: Subject to any disclaimer, the term of this patent is extended or adjusted under 35 U.S.C. 154(b) by 417 days.

(21) Appl. No.: 12/535,218

(22) Filed: Aug. 4, 2009

(65) Prior Publication Data

US 2010/0056810 A1 Mar. 4, 2010

Related U.S. Application Data

(60) Provisional application No. 61/092,191, filed on Aug. 27, 2008.

(51) Int. Cl.
*C07D 311/78* (2006.01)
(52) U.S. Cl. ........................... 549/382; 549/381
(58) Field of Classification Search .................. 549/381, 549/382
See application file for complete search history.

(56) References Cited

U.S. PATENT DOCUMENTS 6,506,538 B1  1/2003 Breyne et al.

FOREIGN PATENT DOCUMENTS

JP  2004 210657 A  7/2004

OTHER PUBLICATIONS

Bruce L. Jensen et al.; "A Concise Synthesis of 1-Substituted-2-Tetralones by Selective Diol Dehydration Leading to Ketone Transposition"; Tetrahedron Letters, 41, 2000, 6029-6033.
Oleg I. Kolodiazhnyi; "Methods of Preparation of C-Substituted Phosphorus Ylides and Their Application in Organic Synthesis"; 1997, Russian Chemical Reviews, 66, 225-254.

*Primary Examiner* — Bernard Dentz
(74) *Attorney, Agent, or Firm* — Robert P. Santandrea; Dean Y. Shahriari

(57) ABSTRACT

Described herein are $C_5$-$C_6$ annelated naphthopyrans that possess at least one electron-withdrawing group. The compounds possess desirable properties such as increased fading kinetics. Also described herein are new methods for synthesizing 2H-chromenes annelated at $C_5$-$C_6$. The methods involve less stringent reaction conditions as well as provide increased reaction yields. The methods permit the synthesis of a wide variety of substituted naphthopyrans that can be temperature sensitive, which was not possible with previous synthetic routes.

6 Claims, 3 Drawing Sheets

2H-CHROMENES ANNELATED AT $C_5$-$C_6$ AND METHODS OF MAKING AND USING THEREOF

CROSS-REFERENCE TO RELATED APPLICATIONS

This application claims the benefit of priority under 35 U.S.C. §119(e) of U.S. Provisional Application Ser. No. 61/092,191 filed on Aug. 27, 2008.

BACKGROUND $C_5$-$C_6$ annelated naphthopyrans are photochromic compounds capable of changing colors under the influence of a poly or monochromatic light such as, for example, UV light. The compounds then return to their initial color when the irradiation ceases, or under the influence of temperature and/or a poly- or monochromatic light different from the initial light. $C_5$-$C_6$ annelated naphthopyrans find applications in various fields such as, for example, in the manufacture of ophthalmic lenses, contact lenses, solar protection glasses, filters, camera optics or other optical devices and observation devices, glazing, and decorative objects. 2H-chromenes annelated at $C_5$-$C_6$ in some cases possess a neutral gray or brown color upon UV irradiation, which is particularly interesting when used in photochromic lenses since it does not require the use of a mixture of dyes of different colors to obtain the desired tint. Indeed, dyes of different colors may have different resistance to UV aging, different fading kinetics, or different thermal dependence, which leads to a change in the tint of the lens during its use. For example, in the case of ophthalmic lenses, it is highly desirable that the photochromic article exhibit fast bleaching in the absence of UV light, both for the comfort of vision and for safety reasons (e.g., during driving).

The synthesis of $C_5$-$C_6$ annelated naphthopyrans has been previously described. One approach involves the reaction of a R-substituted 1-phenyl-3,4-dihydro-1H-naphthalene-2-one with cyanoethylacetate, followed by intramolecular Friedel-Craft cyclization to yield a cyano substituted naphthol. Depending on the R substituent, the yield of this reaction may be very low, which ultimately increases the purification time and manufacture costs of the naphthopyran. Moreover, the process involves high temperatures. For example, the Friedel Craft cyclization is carried out at 200° C., and the removal of the cyano group involves elevated temperatures (220° C.), which is problematic with many temperature sensitive substituents such as, for example, electron-withdrawing groups, present on the naphthopyran. Such substituents may be useful in tuning the photochromic properties of the dye. Therefore, it would be desirable to have a synthetic procedure for the preparation of 2H-chromenes annelated at $C_5$-$C_6$ that require less stringent reaction conditions and provide increased yields.

SUMMARY

Described herein are $C_5$-$C_6$ annelated naphthopyrans that possess at least one electron-withdrawing group. The compounds possess desirable properties such as increased fading kinetics. Also described herein are new methods for synthesizing 2H-chromenes annelated at $C_5$-$C_6$. The methods involve less stringent reaction conditions as well as provide increased reaction yields. The methods permit the synthesis of a wide variety of substituted naphthopyrans that can be temperature sensitive, which was not possible with previous synthetic routes. The advantages of the invention will be set forth in part in the description which follows, and in part will be obvious from the description or the claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
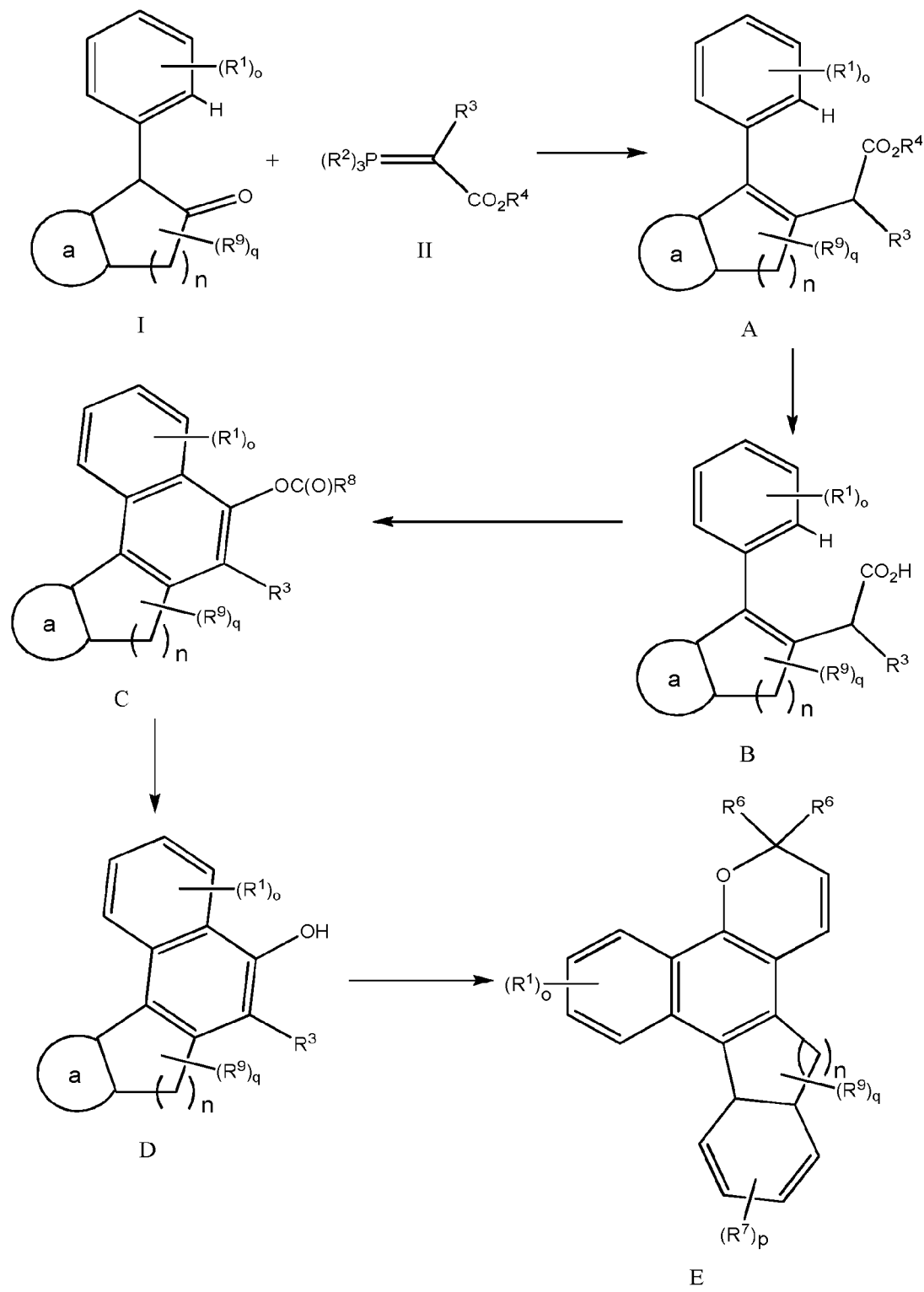
FIG. 1 shows a general reaction scheme for synthesizing 2H-chromenes annelated at $C_5$-$C_6$ using the methods described herein.

Before the present compounds, compositions, articles, devices, and/or methods are disclosed and described, it is to be understood that the examples described below are not limited to specific compounds, synthetic methods or uses as such may, of course, vary. It is also to be understood that the terminology used herein is for the purpose of describing particular examples only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a solvent" includes mixtures of two or more such solvents, and the like unless specified otherwise.

"Optional" or "optionally" means that the subsequently described event or circumstance can or cannot occur, and that the description includes instances where the event or circumstance occurs and instances where it does not.

The term "halogen" is defined herein as fluorine, chlorine, or bromine.

The term "alkyl group" as used herein is a branched or unbranched saturated hydrocarbon group of 1 to 12 carbon atoms such as, for example, methyl, ethyl, n-propyl, isopropyl, n-butyl, isobutyl, t-butyl, pentyl, hexyl, heptyl, octyl, and decyl.

The term "alkoxy" is defined herein as —OR', where R is an alkyl group as defined herein.

The term "aryloxy" is defined herein as —OR', where R' is an aryl group as defined herein.

The term "cycloalkyl group" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl group" is a cycloalkyl group as defined above where at least one of the carbon atoms of the ring is substituted with a heteroatom such as, but not limited to, nitrogen, oxygen, sulphur, or phosphorus.

The term "haloalkyl group" is defined herein as an alkyl group as defined above where at least one hydrogen atom is substituted with a halogen. For example, an alkyl group can have at least one hydrogen atom substituted with fluorine.

Alternatively, all of the hydrogen atoms on the alkyl group can be substituted with fluorine.

The term "halocycloalkyl group" is defined herein as an alkyl group as defined above where at least one hydrogen atom is substituted with a halogen.

The term "haloalkoxy" is defined herein as —OR, where R is an alkyl group as defined herein with at least one hydrogen atom substituted with a halogen.

The term "aryl group or aromatic ring" as used herein is any carbon-based aromatic group including, but not limited to, benzene, naphthalene, etc. The term "aryl or aromatic" also includes "heteroaryl group," which is defined as an aryl or aromatic group that has at least one heteroatom incorporated within the ring of the aryl or aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, aryl, halogen, nitro, amino, ester, ketone, aldehyde, hydroxy, carboxylic acid, or alkoxy.

The term "aralkyl group" is defined herein as an aryl group substituted with an alkyl group.

The term "heteroaralkyl group" is defined herein as a heteroaryl group substituted with an alkyl group. Alternatively, a heteroaralkyl group also includes a heteroalkyl group attached to an aryl group.

The term "phenoxy group" is defined herein as a phenyl group having at least one alkoxy or aryloxy group defined herein. The phenyl ring can be unsubstituted or substituted with one or more additional groups such as, for example, an alkyl group.

The term "naphthoxy group" is defined herein as a naphthenyl group having at least one alkoxy or aryloxy group defined herein. The naphthenyl ring can be unsubstituted or substituted with one or more additional groups such as, for example, an alkyl group.

The term "amine group" is defined herein as —NRR', where R and R' are, independently, an alkyl group, aryl group, cycloalkyl group, a haloalkyl group, a halocycloalkyl group, an aralkyl group, a heteroaralkyl group, a phenoxy group, or a naphthoxy group. This list is not intended to be limiting, as R and R' can be other organic groups. Alternatively, R and R' can form a ring. For example, —NRR' can be part of a 5-, 6-, or 7-membered ring.

The term "halogen" use herein includes fluorine, chlorine, or bromine.

The term "ester" use herein has the formula —COOR', wherein R' is an alkyl group or aryl group as defined herein.

The term "keto" use herein has the formula —C(O)R', wherein R' is an alkyl group or aryl group as defined herein.

The term "amide" use herein has the formula C(O)NR'R", wherein R' and R" are, independently, hydrogen, an alkyl group, or aryl group as defined herein.

The term "sulfone" use herein has the formula —S(=O)(=O)—R', wherein R' is an alkyl group or aryl group as defined herein.

Variables such as $R^1$-$R^9$, a, n, o, p, q, and r used throughout the application are the same variables as previously defined unless stated to the contrary.

The present invention will now be described with specific reference to various examples. The following examples are not intended to be limiting of the invention and are rather provided as exemplary embodiments. Described herein are methods for synthesizing 2H-chromenes annelated at $C_5$-$C_6$. A general reaction scheme for synthesizing the 2H-chromenes is shown in FIG. 1, with a specific reaction sequence provided in FIG. 2.

Referring to FIG. 1, the first step involves reacting ketone I with an ylide having the structure II to produce the ester compound A. The reaction is generally referred to as a Wittig reaction. In a Wittig reaction, the ylide II reacts with the carbonyl group of I to produce A' shown below, which subsequently isomerizes to the more stable structure A

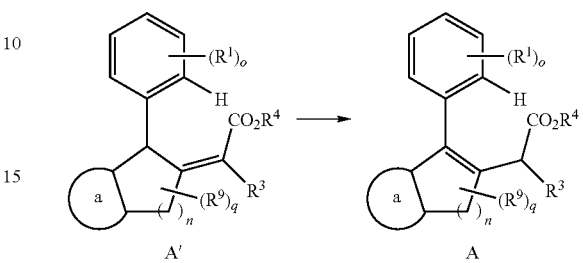

Methods for preparing the ketone I are known in the art. For example, the methods disclosed in U.S. Pat. No. 6,506,538 and B. L. Jensen, S. V. Slobodzian, *Tetrahedron Letters*, 2000, 41, 6029, which are incorporated by reference, can be used to make the ketone I. In one aspect, n is one or two. In the case when n is one, the ring is a five-membered ring, and when n is two, the ring is a six-membered ring. In another aspect, $R^1$ can be, independently, hydrogen, a linear or branched alkyl group, a cycloalkyl group, a linear or branched alkoxy group, a haloalkyl group, a halocycloalkyl group, a haloalkoxy group, an aryl or heteroaryl group, an aralkyl or heteroaralkyl group, a substituted or unsubstituted phenoxy or naphthoxy group, an amine group, an amide group, a —OC(O)$R^5$ or —COO$R^5$ group, wherein $R^5$ can be a straight or branched alkyl group, a cycloalkyl group, an aryl group, or an electron-withdrawing group. The number of $R^1$ groups can be from 1 to 4. In certain aspects, when two adjacent $R^1$ groups are present, together they can form at least one aromatic or non-aromatic cyclic group including a single ring or two annelated rings. For example, a cycloalkyl group such as cyclohexyl or an aryl group such as phenyl can be fused to the aryl ring in ketone I. In a further aspect, each $R^9$ in A is, independently, hydrogen, a hydroxyl group, an alkyl group, an aryl or an alkoxy group, and q is from 1 to 3. In certain aspects, when two adjacent $R^9$ groups are present, together they may form at least one aromatic or non-aromatic cyclic group, optionally substituted with at least one substituent.

Referring to ketone I, a is a substituted or unsubstituted fused aromatic ring. The aromatic ring can be one ring (e.g., phenyl) or multiple rings fused together (e.g, naphthalene, anthracene, etc.). The aromatic ring can be unsubstituted or substituted with one or more $R^1$ groups described above. It is also contemplated that the aromatic group can be a heteroaryl group as defined herein.

In one aspect, with respect to ketone I, a is a substituted or unsubstituted phenyl ring; $R^1$ is a haloalkyl group; n is 2; and o is 1. In another aspect, a is a substituted or unsubstituted phenyl ring; $R^1$ is a trifluoromethyl group; n is 2; and o is 1.

The ylide having the formula II in FIG. 1 is not limited in structure. In one aspect, $R^2$ and $R^4$ can be, independently, an alkyl group, cycloalkyl group, or aryl group. In another aspect, $R^3$ can be hydrogen, an alkyl group, cycloalkyl group, or aryl group. In another aspect, $R^2$ is a phenyl group; $R^3$ is hydrogen; and $R^4$ is an alkyl group (e.g., methyl, ethyl, or the like). The synthesis of ylides having the formula II for use in Wittig reactions is known in the art (see "Phosphrous Ylides: Chemistry and application in Synthesis" by Oleg I. Kolodiazhnyi, Wiley-VCH, New York, 1999; and "Methods for the preparation of C-substituted phosphorus ylides and their application in synthesis" Oleg I Kolodiazhnyi, *Russ. Chem. Rev.*, 1997, 66, 225-254).

The conditions for performing the Wittig reaction are relatively mild. For example, the ketone I and the ylide II can be added to an appropriate organic solvent and heated for a sufficient time to complete the reaction. Detailed experimental procedures for performing the Wittig reaction are provided in the Examples.

Referring to FIG. 1, the next step involves hydrolysis of compound A to produce compound B. It is understood that any compound having formula A can be used as the starting material for the hydrolysis step. The hydrolysis step is generally conducted under mild conditions. In one aspect, the hydrolysis step is conducted at a temperature less than 100° C. and less than two hours. In another aspect, the hydrolysis step is performed at about 80° C. for about an hour. The reaction conditions of the first two steps of the present invention are considerably milder than prior art techniques. For example, the techniques disclosed in U.S. Pat. No. 6,506,538 involve the reaction of a R-substituted 1-phenyl-3,4-dihydro-1H-naphthalene-2-one with cyanoethylacetate, followed by intramolecular Friedel-Craft's cyclization to yield a cyano substituted naphthol. The Friedel-Crafts reaction is carried out at 200° C., and the hydrolysis of the ester and removal of the cyano group involves even higher temperatures (220° C.), which is problematic with temperature-sensitive substituents. The whole process takes more than 24 hours at high temperatures. Moreover, depending on the R substituent, the yield of the reaction may be very low, which increases the purification time and the manufacturing cost of the material. Conversely, the first two steps described herein are substantially milder, with lower reaction times and temperatures and increased yields for compound B (e.g., 85-92%).

The next step involves performing a Friedel-Crafts cyclization of a compound having the formula B to produce compounds having the formula C. Conditions for conducting the Friedel-Crafts cyclization are known in the art. The cyclization can be carried out under a variety of conditions. In general, the cyclization is carried out in presence of a Lewis acid such as, for example, $AlCl_3$, $TiCl_4$ or $BF_3.Et_2O$. Depending on the substituents present on formula B, different Lewis acids ranging from highly acidic to very mild can be used. In one aspect, the cyclization step is performed in the presence of an anhydride and the sodium salt of the anhydride. For example, the cyclization is carried out in the presence of $Ac_2O/NaOAc$, where $R^8$ in the formula C is methyl, which is derived from the acetyl group from the reactants. $R^8$ can be other alkyl groups as defined herein.

In one aspect, after the cyclization step is performed to produce compounds having the formula C, the compound is subjected to a second hydrolysis step to produce a compound having the structure D (FIG. 1), where the acetyl group is converted to the hydroxyl group. Similar to the first hydrolysis step described above, the second hydrolysis step requires only mild conditions. In one aspect, the second hydrolysis step is conducted at a temperature less than 100° C. and less than two hours. In another aspect, the hydrolysis step is performed at about 80° C. for about an hour. As described above, previous synthetic techniques hydrolyse and remove the cyano group in a one pot reaction under rigid conditions (e.g., potassium hydroxide in n-butanol at high temperature of 200-220° C. for 6 hours). Moreover, the work-up of the reaction is cumbersome and results in low yields. The methods described herein for producing compounds having the formula D involve much milder conditions (e.g., use of methanolic solution of sodium hydroxide at 80° C. for one hour).

The hydrolysis product D can also be obtained in very high yields (e.g., range of 75% to quantitative yield).

The methods described herein provide a convenient way to produce compounds useful in the production of $C_5$-$C_6$ annelated naphthopyrans. As described above, this class of compounds has a wide variety of applications, and the methods described herein provide access to a number of different compounds that could not be produced or only produced in relatively low yields using existing synthetic techniques. With easy access to compounds having the structure D, it is possible to use techniques known in the art to produce a number of substituted photochromic compounds having the formula E (FIG. 1). For example, a compound having the formula D can be reacted with the propargyl alcohol F to produce compounds having the structure E,

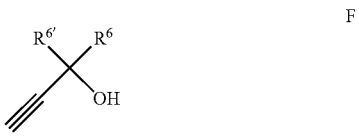

F where $R^6$ and $R^{6'}$ are, independently, a linear or branched alkyl group, a cycloalkyl group, a linear or branched alkoxy group, a haloalkyl group, a halocycloalkyl group, a haloalkoxy group, an aryl or heteroaryl group, an aralkyl or heteroaralkyl group, or a substituted or unsubstituted phenoxy or naphthoxy group. Experimental procedures for this reaction are provided in the Examples and U.S. Pat. No. 6,506,538.

The methods described herein permit the synthesis of compounds having the formula E with sensitive groups (e.g., electron-withdrawing groups) that could not be produced by other techniques. For example, prior art techniques that employ high temperatures and alkaline conditions would hydrolyze fluoroalkyl and cyano groups at $R^1$ in formula E. Moreover, high reaction yields at each step of the synthesis are possible using the methods described herein. For example, Table 1 in the Examples provides reaction yields for four different reaction series.

Also described herein are unique compounds produced by the methods described above. For example, compounds having the formula A-D are new and useful compounds produced as a result of the methods described herein. In one aspect, when the compound has the formula A, a is a substituted or unsubstituted phenyl ring; $R^1$ is a haloalkyl group such as, for example, a trifluoromethyl group; n is 2; o is 1; $R^3$ is hydrogen; and $R^4$ is an alkyl group. In another aspect, when the compound has the formula B, a is a substituted or unsubstituted phenyl ring; $R^1$ is a haloalkyl group such as, for example, a trifluoromethyl group; n is 2; o is 1; and $R^3$ is hydrogen. In a further aspect, when the compound has the formula C, a is a substituted or unsubstituted phenyl ring; $R^1$ is a haloalkyl group such as, for example, a trifluoromethyl group; n is 2; o is 1; and $R^3$ is hydrogen. In another aspect, when the compound has the formula D, a is a substituted or unsubstituted phenyl ring; $R^1$ is a haloalkyl group such as, for example, a trifluoromethyl group; n is 2; o is 1; and $R^3$ is hydrogen.

In one aspect, the methods described herein can produce compounds having the formula G

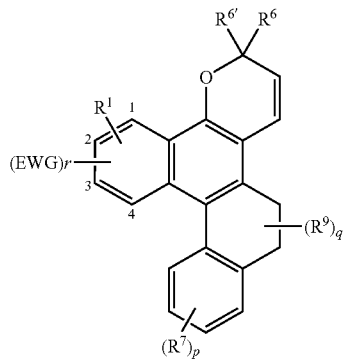

wherein
R¹ is hydrogen, a linear or branched alkyl group, a cycloalkyl group, a linear or branched alkoxy group, an aryl or heteroaryl group, or an aralkyl or heteroaralkyl group;
EWG is an electron-withdrawing group;
p is from one to four;
q is one or two;
r is from one to three;
each $R^6$, $R^{6'}$, and $R^7$ are, independently, a linear or branched alkyl group, a cycloalkyl group, a linear or branched alkoxy group, a haloalkyl group, a halocycloalkyl group, a haloalkoxy group, an aryl or heteroaryl group, an aralkyl or heteroaralkyl group, or a substituted or unsubstituted phenoxy or naphthoxy group; and
each $R^9$ is, independently, hydrogen, a hydroxyl group, an alkyl group, an aryl or an alkoxy group, wherein when two adjacent $R^9$ groups are present, they may form at least one aromatic or non-aromatic cyclic group, optionally substituted with at least one substituent.

The compounds having the formula G have at least one electron-withdrawing group (EWG) at C1, C2, C3, or C4. The term "electron-withdrawing group" as used herein is any group that removes or pulls electron density from the aromatic ring, thus rendering the aromatic ring electron deficient when compared to the same aromatic ring that does not possess the electron-withdrawing group. Examples of electron-withdrawing groups include, but are not limited to, a halogen, a nitro group, a cyano group, an ester group, an aldehyde group, a keto group, a sulfone group, an amide group, a haloalkyl group, or a halocycloalkyl group.

In certain aspects, the electron-withdrawing group is at C2 or C3 in formula F. In one aspect, the electron-withdrawing group is a haloalkyl groups such as, for example, a trifluoromethyl group at C2 or C3. In other aspects, the electron-withdrawing group is a keto group having the formula —C(O)R⁵ at C2 or C3, wherein R⁵ is a straight or branched alkyl group or aryl group.

The other groups in formula F can vary depending upon the application of the compound. In one aspect, R¹ is hydrogen or an alkoxy group. In another aspect, R¹ is hydrogen or an alkoxy group, p is one, and R⁷ is hydrogen or an alkoxy group. In a further aspect, R¹ is hydrogen or an alkoxy group, p is one, R⁷ is hydrogen or an alkoxy group, q is one, and R⁹ is hydrogen.

In one aspect, the electron-withdrawing group is a trifluoromethyl group at C2 or C3, R¹ is hydrogen, p is one, R⁷ is hydrogen or an alkoxy group, q is one, R⁹ is hydrogen, and each R⁶ is, independently, an aryl or heteroaryl group. In another aspect, the electron-withdrawing group is —C(O)R⁵ at C2 or C3, wherein R⁵ is a straight or branched alkyl group or aryl group, R¹ is hydrogen or an alkoxy group, p is one, R⁷ is hydrogen or an alkoxy group, q is one, R⁹ is hydrogen, and each R⁶ is, independently, an aryl or heteroaryl group. Additional examples of compounds having the formula G as well as specific reaction conditions are provided in the Examples below.

The compounds having the formula G have desirable photochromic properties. For example, the compounds exhibit fast fading kinetics. In one aspect, the compounds have increased fading kinetics compared to similar compounds without the electron-withdrawing group. For example, the compounds dispersed in an acrylic matrix having the composition described in the examples have fading kinetics as measured by the half time of fading ($t_{1/2}$) of 10 seconds to 35 seconds. This is significantly lower than the value of $t_{1/2}$ with no electron-withdrawing group, which can be about 70 seconds to 80 seconds in the same matrix. Techniques for measuring the fading kinetics are provided in the Examples. Additionally, the presence of the electron-withdrawing group has little influence on the color of the compound in the activated state.

The compounds having the formula G can be incorporated into a variety of polymeric matrices, which can ultimately be used to produce a variety of different articles. In general, the polymer matrix with the compound having the formula G incorporated therein or coated thereon is colorless or slightly colored in the initial state and rapidly develops intense coloration when exposed to UV light (365 nm) or under a light source of the solar type. Finally, the polymeric matrix regains its initial coloration once the irradiation ceases. The compound having the formula G can be used alone or in combination with other photochromic materials. It is also contemplated that two or more compounds having the formula G can be used to make the article.

Examples of polymers useful herein include, but are not limited to, alkyl, cycloalkyl, (poly or oligo)ethylene glycol, aryl or arylalkyl mono-, di-, tri- or tetraacrylate or mono-, di-, tri- or tetramethacrylate, which is optionally halogenated or which includes at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral. Homopolymers and copolymers derived from the materials described above can be used herein.

The compounds having the formula G can be incorporated in or applied to any article where it is desirable to prevent exposure or entry of sunlight. In one aspect, the article can be an ophthalmic lens, a photochromic solar lenses, glazing (windows for buildings, for locomotion engines, automotive vehicles, and the like), optical devices, decorative articles, and solar protection articles.

EXAMPLES

The methods described herein will now be discussed with specific reference to various examples. The following examples are not intended to be limiting of the invention and are rather provided as exemplary embodiments. Efforts have been made to ensure accuracy with respect to numbers (e.g., amounts, temperatures, etc.); however, some errors and deviations may have occurred. Unless indicated otherwise, parts are parts by weight, temperature is ° C. or is at ambient temperature, and pressure is at or near atmospheric.

Figure 2:
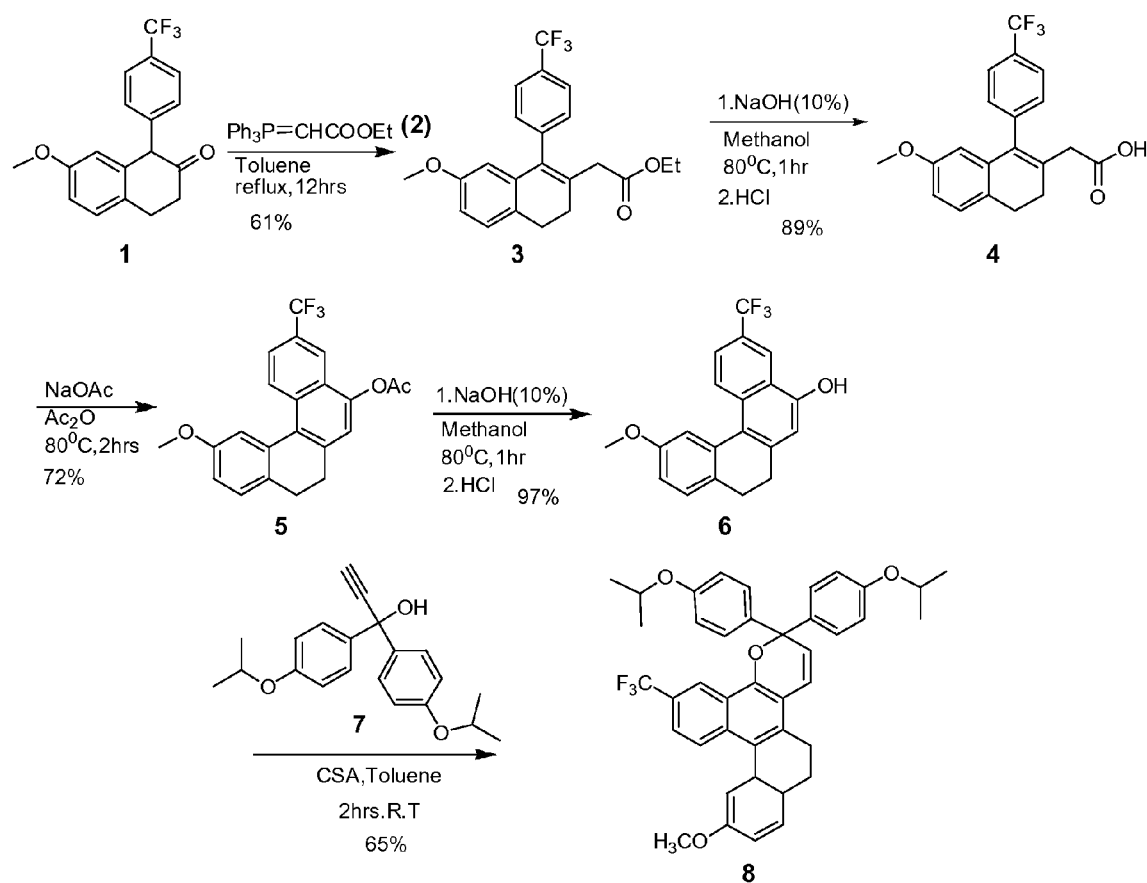
FIG. 2 shows an exemplary reaction scheme for synthesizing 2H-chromenes annelated at $C_5$-$C_6$ using the methods described herein.

I. Preparation of $C_5$-$C_6$ Annelated Naphthopyrans Using the Methods Described Herein All numbering referred to below is shown in FIG. 2. Table 1 provides reaction yields of steps 1-5 described below for four different series of compounds.

Step 1: Wittig Reaction

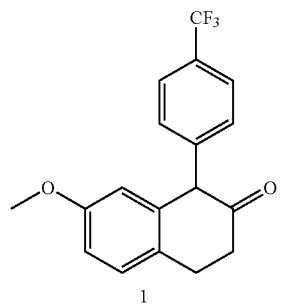

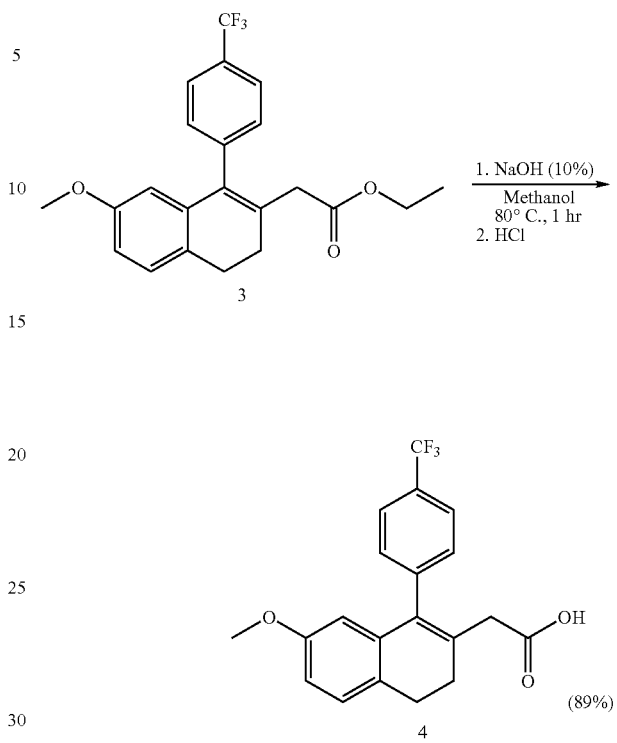

In a two necked flask fitted with a reflux condenser and Argon balloon, the ketone 1 (1.7 g, 5.3 mmoles) and the Wittig ylide 2 (3.7 g, 10.6 mmoles) were placed in dry toluene (20 ml) and refluxed at 130° C. (oil bath temp) for 12 hrs. Toluene was then removed under vacuum and the mixture was purified by column chromatography on a column of silica gel using a mixture of hexane-ethyl acetate (97:3) which gave 61% (1.26 g, 3.3 mmoles) of the isomerised olefin ester adduct 3. FT-IR (KBr, $\upsilon_{max}$/cm$^{-1}$): 1107, 1156, 1328, 1499, 1604, 1724, 2833, 2928. $^1$HNMR (300 MHz, CDCl$_3$): δ 1.23 (t, 3H, J=7.1), 2.46 (t, 2H, J$_1$=8.3 Hz, J$_2$=7.5 Hz), 2.86 (t, 2H, J$_1$=7.4 Hz, J$_2$=8.2 Hz), 3.04 (s, 2H), 3.64 (s, 3H), 4.11 (q, 2H, J=14.3 Hz), 6.09 (d, 1H, J=2.6 HZ), 6.67 (dd, 1H, J$_1$=8.2 Hz, J$_2$=2.6 Hz), 7.09 (d, 1H, J=8.2 Hz), 7.33 (d, 2H, J=7.9 Hz), 7.66 (d, 2H, J=7.9 Hz). $^{13}$CNMR (75 MHz, CDCl$_3$): δ 14.14, 27.16, 28.67, 40.63, 55.17, 60.73, 110.98, 112.88, 125.41, 127.46, 127.88, 28.95, 129.25, 130.51, 131.76, 135.89, 136.72, 142.74, 158.16, 170.96. LRMS (FAB): calculated for $C_{22}H_{21}O_3F_3$ 390.40; m/z found 390.86.

Step 2: Hydrolysis of the Wittig Adduct

The Wittig adduct 3 (1.4 g, 3.58 mmoles) was dissolved in methanol (15 ml), mixed with NaOH solution (10% aqueous, 3 ml), and refluxed at 80° C. for an hour. Methanol was removed under reduced pressure and the mixture was then acidified with concentrated HCl (1 ml). The precipitated residue was extracted with ethyl acetate, washed with water, dried over sodium sulphate and purified on a column of silica gel using ethyl acetate/hexane (20:80) to produce acid 4 at 89% yield (1.15 g, 3.18 mmoles) as a white crystalline solid. FT-IR (KBr,$\upsilon_{max}$/cm$^{-1}$): 1240, 1327, 1498, 1687, 2934. $^1$HNMR (300 MHz, CDCl$_3$.): δ 2.48 (t, 2H, J$_1$=8.1, J$_2$=7.5 Hz), 2.87 (t, 2H J$_1$=7.5 J$_2$=7.7 Hz), 3.09 (s, 2H), 3.63 (s, 3H), 6.09 (s, 1H), 6.68 (d, 1H, J=10.3 Hz), 7.09 (d, 1H, J=8.2 Hz), 7.33 (d, 2H, J=7.7 Hz), 7.67 (d, 2H, J=8.01 Hz). $^{13}$CNMR (75 MHz, CDCl$_3$): δ 27.10, 28.63, 40.24, 55.20, 111.19, 112.99, 125.52, 125.57, 127.44, 127.94, 129.39, 130.42, 130.72, 136.51, 142.49, 158.16, 177.34. LRMS (FAB): Calculated for $C_{20}H_{17}F_3O_3$: 362.34; found: 363.76 (M+1)

Step 3: Friedel-Craft's Cyclization

-continued

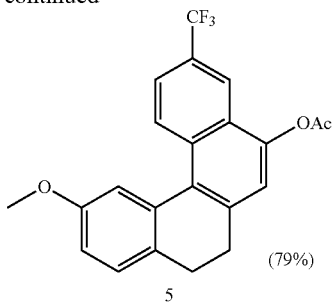

(79%)

5

Acid 4 (1.1 g, 3.04 mmoles) was mixed with acetic anhydride (5 ml) and sodium acetate (498 mg, 6.07 mmoles) and the mixture was heated at 80° C. for 3 hours. The crude mixture was then diluted with water, extracted with ethyl acetate and neutralized with solid sodium bicarbonate to remove all of the acetic acid. The organic layer was washed with water, dried over anhydrous sodium sulphate, and concentrated under vacuum. The residue was purified on a column of silica gel using ethylacetate/hexane (5:95) to yield 79% of the acylated naphthol 5 (0.930 g, 2.40 mmoles) as a sticky solid. FT-IR (neat, $\upsilon_{max}/cm^{-1}$): 1114, 1155, 1205, 1315, 1375, 1598, 2951, 3327. $^1$HNMR (300 MHz, CDCl$_3$): δ 2.5 (s, 3H), 2.76 (t, 2H J$_1$=6.6 Hz, J$_2$=5.7 Hz), 2.89 (t, 2H J$_1$=5.6 Hz, J$_2$=6.6 Hz), 3.84 (s, 2H), 6.85 (dd, 1H, J$_1$=8.2 Hz, J$_2$=2.5 Hz), 7.24-7.45 (m, 3H), 7.67 (d, 1H, J=9.02 Hz), 8.20 (s, 1H), 8.68 (d, 1H, J=9.03 Hz). $^{13}$CNMR (75 MHz, CDCl$_3$): δ21.07, 28.09, 30.96, 55.44, 112.12, 115.12, 119.49, 120.04, 122.12, 125.81, 126.05, 127.04, 127.37, 128.54, 130.19, 131.48, 132.18, 133.89, 139.80, 145.88, 158.00, 169.37. LRMS (FAB): Calculated for C$_{22}$H$_{17}$F$_3$O$_3$: 386.36; found 386.78.

Step 4: Hydrolysis of the Acylated Naphthol

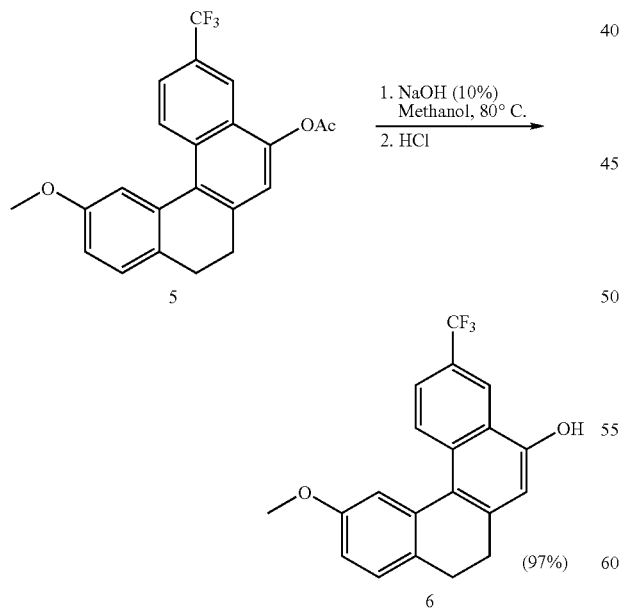

Acylated naphthol 5 (930 mg, 2.40 mmoles) was dissolved in methanol (10 ml) then mixed with NaOH solution (10% aqueous, 3 ml) and refluxed at 80° C. for one hour. Methanol was removed under vacuum and the mixture was then acidified with concentrated HCl (0.5 ml). The precipitated naphthol 6 was extracted with ethyl acetate, washed with water, dried over sodium sulphate, and purified on a column of silica gel using ethyl acetate/hexane (10:90) to provide 6 in 97% yield (0.818 g, 2.38 m moles) as a white solid. FT-IR (KBr, $\upsilon_{max}/cm^{-1}$): 1114, 1155, 1205, 1315, 1375, 1598, 2951, 3327. $^1$HNMR (300 MHz, CDCl$_3$): δ 2.80 (m, 4H), 3.86 (s, 3H), 5.78 (s, 1H), 6.79-6.84 (m, 2H), 7.28 (s, 1H), 7.37 (d, 1H, J=2.4 Hz), 7.65 (d, 1H, J=7.5 Hz), 8.62 (t, 2H, J$_1$=9 Hz, J$_2$=12.1 Hz). $^{13}$CNMR (75 MHz, CDCl$_3$): δ 28.26, 31.18, 55.46, 110.48, 111.33, 114.50, 120.40, 120.46, 122.19, 123.38, 125.00, 125.80, 126.26, 128.32, 131.08, 132.41, 134.52, 140.49, 151.26, 157.98. LRMS (FAB): Calculated for C$_{20}$H$_{15}$F$_3$O$_2$:344.33; found 344.69.

Step 5: Final Condensation

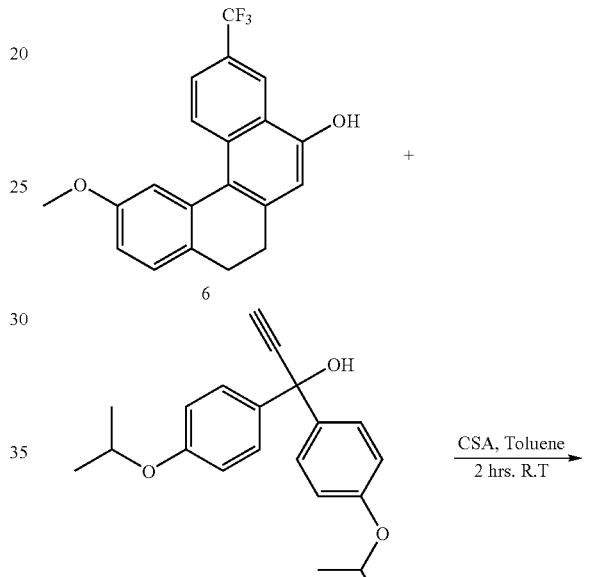

In a 100 ml round bottomed flask a mixture of naphthol 6 (150 mg, 0.43 mmol) and 7 (155.4 mg, 0.48 mmol) was dissolved in benzene (10 mL). To this mixture, camphor sulfonic acid (20 mg) was added and stirred at room temperature for 3 hrs. After completion of the reaction as monitored by TLC, evaporation of excess solvent followed by column chromatographic purification of the crude material yielded 270 mg of 8 in (95%) yield. FT-IR (neat,$\upsilon_{max}/cm^{-1}$): 1123, 1180, 1247, 1317, 1370, 1506, 1607, 2980. $^1$H NMR (300 MHz, CDCl$_3$,): δ 1.29 (d, 12H, J=5.9 Hz), 2.70-2.85 (m, 4H), 3.80 (s, 3H), 4.45-4.53 (m, 2H), 6.21 (d, 1H, J=9.9 Hz), 6.76-6.83 (m, 5H), 6.93 (d, 1H, J=10.0 Hz), 7.22-7.26 (m, 2H), 7.36 (d, 4H, J=8.7 Hz), 7.56 (d, 1H, J=7.3 Hz), 8.52 (d, 1H, J=8.7 Hz), 8.65 (s, 1H). $^{13}$CNMR (75 MHz, CDCl$_3$): δ 21.99, 26.07, 28.00, 29.03, 55.32, 69.71, 82.83, 119.46, 120.32, 121.76, 123.53, 125.31, 126.20, 126.39, 126.63, 128.08, 128.23, 129.28, 130.59, 131.99, 134.68, 136.42, 136.64, 147.86, 157.43, 157.97. LRMS (FAB): Calculated for C$_{41}$H$_{39}$F$_3$O$_4$ 652.28: found 652.17.

TABLE 1

Yields for Steps 1-5

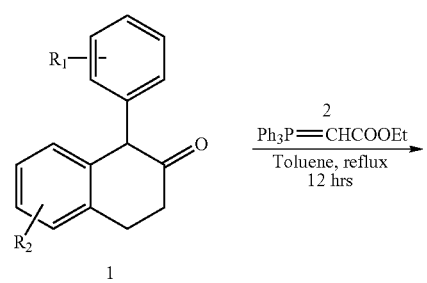

1

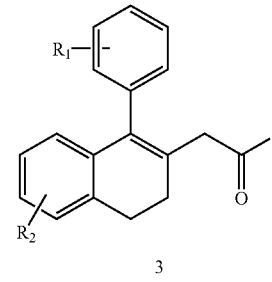

3

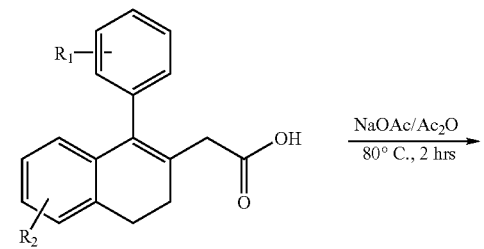

4

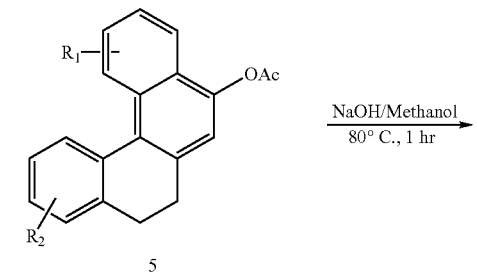

5

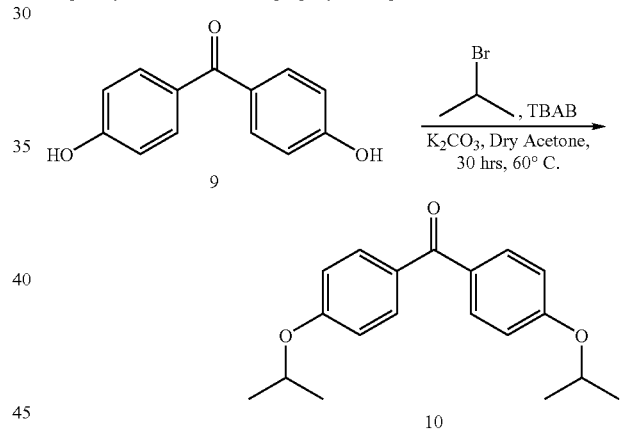

6

TABLE 1-continued

| Entry | Yield in each step | | | |
|---|---|---|---|---|
| | 3 | 4 | 5 | 6 |
| 1 R$_1$ = 4-(CF$_3$)—<br>R$_2$ = 7-(methoxy) | 61 | 89 | 79 | 97 |
| 2 R$_1$ = 4-(CF$_3$)—<br>R$_2$ = H | 75 | 91 | 91 | 91 |
| 3 R$_1$ = 4-(OPh)—<br>R$_2$ = H | 54 | 83 | 77 | 81 |
| 4 R$_1$ = 3-(CF$_3$)—<br>R$_2$ = H | 75 | 92 | 70 | 77 |

II. Preparation of Methoxy Substituted C$_5$-C$_6$ Annelated Naphthopyrans

Step 1: Synthesis of 4,4'-Diisopropoxy Benzophenone

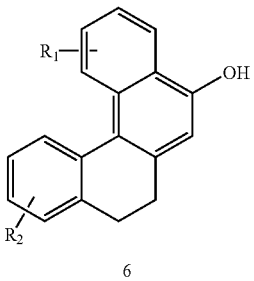

9

10

Compound 9 (1 g, 4.6 mmol) was dissolved in 20 mL dry acetone in a 100 mL round bottom flask fitted with a reflux condenser. To this mixture K$_2$CO$_3$ (3.2 g, 5 eq., 9.33 mmol), isopropylbromide (10 equiv., 46 mmol) and tetrabutylammonium bromide (TBAB) (0.5 eq.) were added. The mixture was refluxed for 30 hrs at 60° C. When the reaction was complete (monitored by TLC), acetone was removed under reduced pressure on a rotary evaporator; diluted with distilled water and extracted with ethyl acetate (25 mL×3). The organic layer was separated, washed with brine and dried over anhydrous Na$_2$SO$_4$. Evaporation of the solvent followed by column chromatographic purification of the crude material yielded compound 10 in 82% yield as a white solid.

The product was characterized by the following spectral techniques. FT-IR(KBr,υ$_{max}$/cm$^{-1}$): 2980, 2935, 2900, 1676, 1639, 1598, 1504, 1467, 1454, 1377, 1255, 950, 848. $^1$H NMR (300 MHz, CDCl$_3$): δ 7.76 (d, 4H, J=8.79 Hz), 6.93 (d, 4H, J=8.79 Hz), 4.68-4.64 (m, 2H), 1.30-1.39 (s, 12H). $^{13}$C NMR (75 MHz, CDCl$_3$): δ 161.04, 131.95, 130.10, 114.62, 69.74, 21.67

Step 2: Synthesis of propargyl alcohol 11

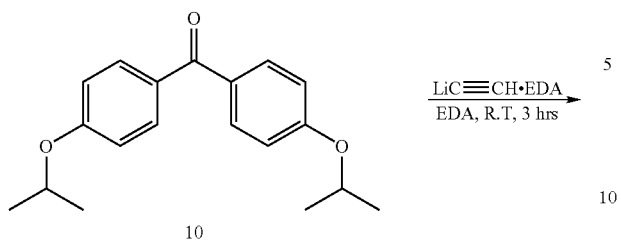

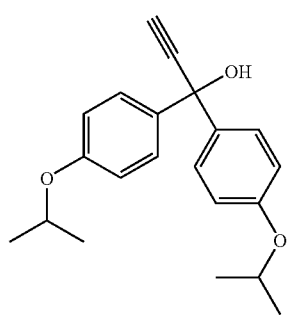

Ketone 10 (200 mg, 6.71 mmol) was dissolved in 5 mL ethylenediamine, and lithium acetylide (3 eq, 2.01 mmol) was added to it. The reaction mixture was stirred at room temperature for 3 hrs under Argon atmosphere. After the completion of reaction, as monitored by TLC, the reaction mixture was quenched with ice-water and extracted with a mixture of ethyl acetate, diisopropyl ether and toluene in a 4:3:3 ratio. The organic layer was washed with water, followed by brine and dried over anhydrous sodium sulfate. The solvent was evaporated by vacuum and the crude product was purified by silica gel column chromatography using hexane/EtOAc mixture (95:5) to yield compound II in 80% overall yield as white solid.

The product was characterized by the following spectral techniques. FT-IR(KBr,$\upsilon_{max}$/cm$^1$): 3450, 3273, 2980, 2360, 1606, 1504, 1367, 1240, 1170, 950, 823. $^1$H NMR (300 MHz, CDCl$_3$): δ 7.49-7.45 (m, 4H), 6.85-6.81 (m, 4H), 4.56-4.48 (m, 2H), 2.8 (s, 1H), 1.32 (s, 12H). $^{13}$C NMR (75 MHz, CDCl$_3$): δ 157.42, 136.57, 127.70, 115.24, 86.68, 74.92, 73.62, 69.79, 22.00. LR-MS (FAB): m/z=found at 323.96, calculated for $C_{21}H_{24}O_3$ 323.17

Step 3: Synthesis of 13

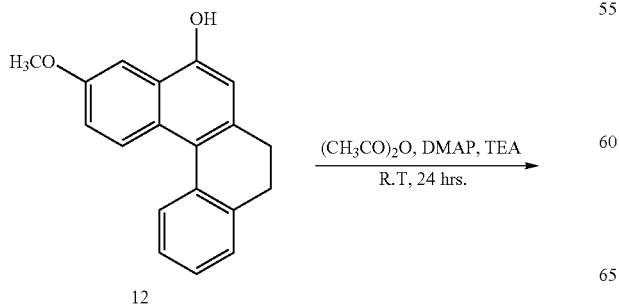

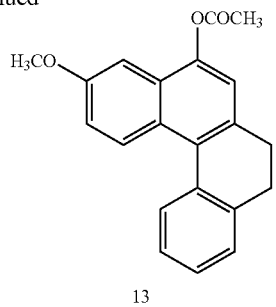

Compound 12 (100 mg, 3.6 mmol) was dissolved in 2 mL of triethlyamine and 0.06 mL of acetic anhydride (2 eq. 7.2 mmol). DMAP (2 mg) were added to the mixture. The mixture was stirred at room temperature for 24 hrs. After the completion of the reaction, as monitored by TLC, work up was done by initially adding water, followed by sodium bicarbonate until the CO$_2$ evolution ceases and the aqueous layer remains basic. The reaction mixture was extracted with chloroform, washed with brine and dried over anhydrous Na$_2$SO$_4$. Evaporation of the solvent under reduced pressure followed by silica gel column chromatographic purification of the crude material yielded compound 13 in 85% yield as white solid.

The product was characterized by the following spectral techniques. FT-IR(KBr,$\upsilon_{max}$/cm$^1$): 2938, 2835, 1763, 1626, 1605, 1509, 1475, 1366, 1197, 1170, 1037, 920, 831. $^1$H NMR (300 MHz, CDCl$_3$): δ 8.45 (d, 1H, J=9.2 Hz), 7.82 (d, 1H, J=7.6 Hz), 7.14-7.36 (m, 6H), 3.94 (s, 3H), 2.83 (s, 4H), 2.48 (s, 3H). $^{13}$C NMR (75 MHz, CDCl$_3$): 169.10, 156.90, 144.32, 139.19, 134.25, 133.39, 129.74, 128.25, 127.76, 127.49, 127.42, 126.57, 126.37, 125.74, 118.91, 118.41, 99.77, 54.75, 29.85, 29.07, 20.56. LR-MS (FAB): m/z=found at 317.96 calculated for $C_{21}H_{18}O_3$ at 316.13

Step 4: Friedel Crafts Acylation of 13

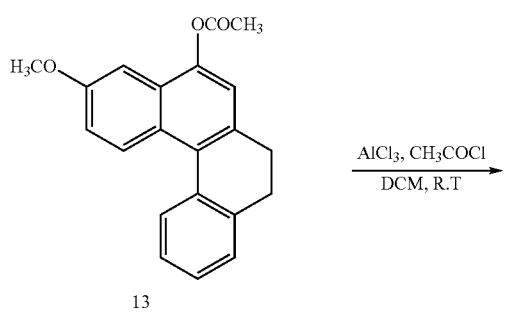

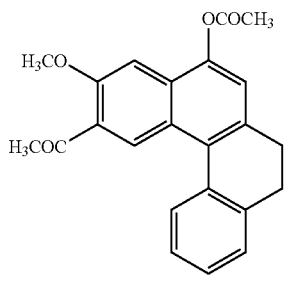

To a solution of compound 13 (100 mg, 3.14 mmol) in dry dichloromethane, anhydrous aluminum chloride (3 eq., 0.94 mmol) was added, followed by the addition of acetyl chloride (0.05 mL, 2 eq., 0.62 mmol), and the mixture was stirred at room temperature for two hours. After the completion of the reaction (monitored by TLC), the reaction was quenched by adding ice and extracted with dichloromethane. The organic layer was separated, washed with brine and dried over anhydrous $Na_2SO_4$. Evaporation of the solvent followed by column chromatographic purification of the crude material yielded compound 14 in (60% yield) as colorless liquid.

The product was characterized by the following spectral techniques. FT-IR(KBr,$\upsilon_{max}$/cm$^1$): 2924, 2851, 1766, 1733, 1677, 1597, 1362, 1260, 1127, 1037, 965, 820. $^1$H NMR (300 MHz, CDCl$_3$): δ 8.38 (d, 1H, J=9.3 Hz), 7.95-7.87 (m, 3H), 7.26-7.17 (m, 3H), 3.94 (s, 3H), 2.87 (s, 4H), 2.65 (s, 3H), 2.49 (s, 3H). LR-MS (FAB): m/z calculated for $C_{23}H_{20}O_4$: 361.14; found: 361.48

Step 5: Base Hydrolysis of Compound 14

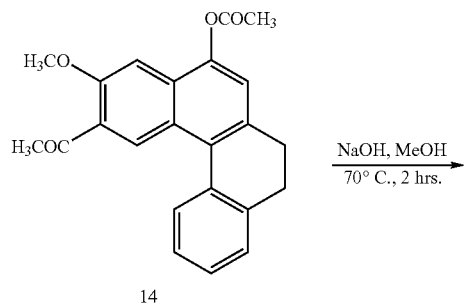

14

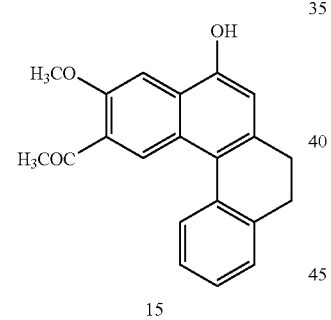

15

To a solution of 14 (80 mg, 0.22 mmol) in methanol (5 mL), 10% NaOH solution (1 ml) was added and the mixture was refluxed for two hours. After the completion of the reaction, as monitored by TLC, work up was done by initially removing the excess solvent under reduced pressure followed by acidification of the aqueous layer using 1% HCl. The mixture was extracted with ether, the organic layer washed with brine and dried over anhydrous sodium sulphate to produce the crude mixture. The crude mixture was purified by chromatography on silica gel to yield compound 15 in 60% overall yield as yellow viscous liquid.

The product was characterized by the following spectral techniques. FT-IR(KBr,$\upsilon_{max}$/cm$^1$): 3258, 2935, 2838, 1614, 1590, 1520, 1496, 1479, 1391, 1357, 1215, 1069, 818, 763. $^1$H NMR (300 MHz, CDCl$_3$): δ 8.36 (d, 1H, J=9.4 Hz), 7.95-7.90 (m, 3H), 7.26-7.18 (m, 3H), 3.98 (s, 3H), 2.83 (s, 4H), 2.65 (s, 3H). LR-MS (FAB): m/z found at 319.46 calculated for $C_{21}H_{18}O_3$ at 319.13

Step 6: Final Condensation

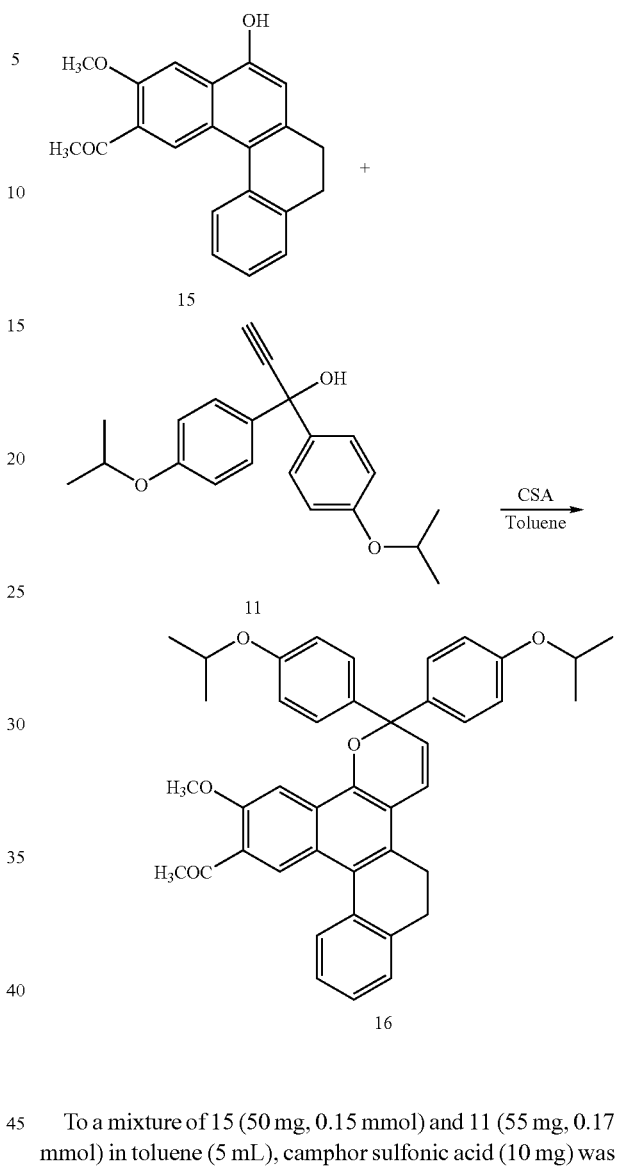

To a mixture of 15 (50 mg, 0.15 mmol) and 11 (55 mg, 0.17 mmol) in toluene (5 mL), camphor sulfonic acid (10 mg) was added and the reaction mixture was stirred at 60° C. for 2 hrs. After completion of reaction, as monitored by TLC, evaporation of the excess solvent followed by column chromatographic purification of the crude material yielded 16 in 56% yield.

Compound 16 was characterized by the following spectral techniques. FT-IR(KBr,$\upsilon_{max}$/cm$^1$): 2932, 2862, 1728, 1602, 1451, 1366, 1248, 1178, 1119, 828, 735. $^1$H NMR (300 MHz, CDCl$_3$): δ 8.25 (d, 1H, J=9.3 Hz), 7.98-7.77 (m, 3H), 7.68 (d, 1H J=2.5 Hz), 7.38 (d, 4H, J=8.7 Hz), 7.14 (m 1H,), 6.94 (d, 1H, J=9.5 Hz), 6.82 (d, 4H, J=8.7 Hz), 6.20 (d, 1H, J=9.8 Hz), 4.53-4.47 (m, 2H), 3.95 (s, 3H), 2.85 (s, 4H), 2.63 (s, 3H), 1.32-1.25 (m, 12H). $^{13}$C NMR (75 MHz, CDCl$_3$): 197.84, 157.24, 156.95, 147.35, 139.46, 138.58, 136.98, 134.32, 132.53, 128.60, 128.19, 127.95, 127.07, 126.54, 126.36, 125.69, 124.32, 119.74, 118.83, 115.02, 113.96, 101.09, 82.43, 69.70, 55.41, 29.31, 29.02, 26.53, 25.19, 22.65. LR-MS (FAB): m/z=found at 625.71 calculated for $C_{42}H_{40}O_5$ at 625.29.

Compound 17 in Table 2 was synthesized according to a similar method as described above for 16.

III. Analysis of Photochromic Properties

Figure 3:
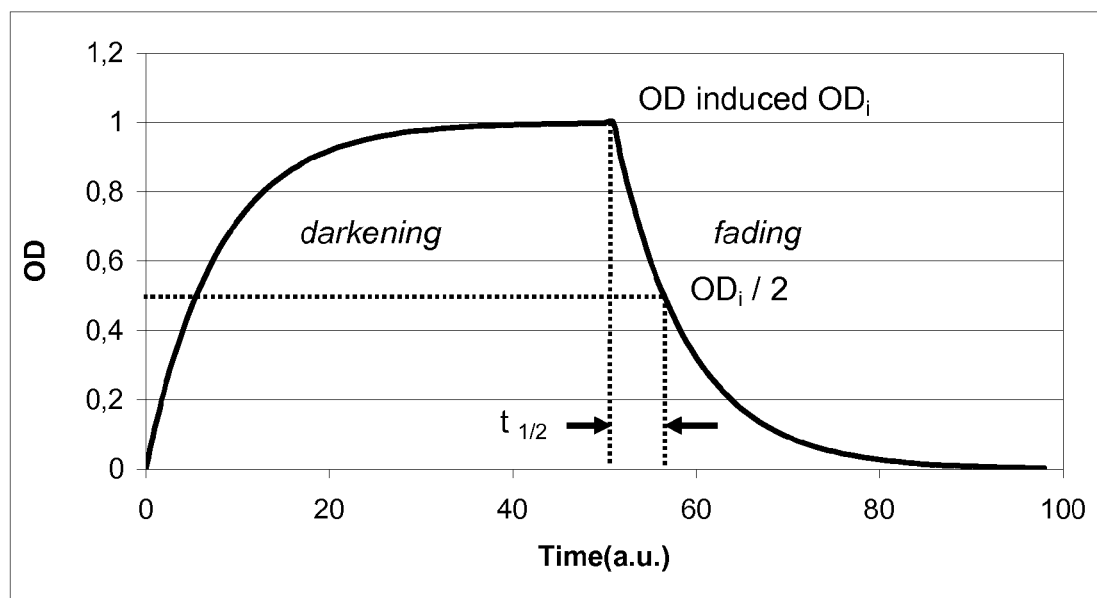
FIG. 3 shows a graph for the determination of $t_{1/2}$ (i.e. the half time of fading) of several compounds described herein.

The photochromic properties of each dye were characterized in 2 mm thick lenses containing a 0.05 wt % dispersion of the dye in a mixture of 10 wt % divinylbenzene, 60 wt % bisphenol A ethoxylate dimethacrylate, 30 wt % poly(ethylene glycol) dimethacrylate, average 550 g/mol, 0.2 wt % 2,2'-azobis(2-methylbutyronitrile), 0.5 wt % dodecanethiol, cast between two glass plates 2 hours at 70° C. and then 2 hours at 90° C. The photochromic characteristics were observed at 22° C. during 5 minutes fading in the dark after 15 minutes of darkening with 82 klux irradiation (AM2 distribution) as shown in FIG. 3. In particular, the fading kinetics were measured by the halftime of fading (t1/2).

As shown in Table 2, the addition of electron withdrawing groups on the naphthyl ring dramatically decreases the half time of fading from 71s down to 16s with little change in the dye color with compounds 16-18.

TABLE 2

| Dye | Comparative Example | 16 | 17 | 18 |
|---|---|---|---|---|
| R = | H | O=C—CH₃ | O=C—C₆H₅ | —CF3 |
| Color | Gray | Gray | Gray | Blue-gray |
| $t_{1/2}$ (s) | 71 | 31 | 23 | 16 |

Different dyes bearing electron withdrawing —CF3 substituents on the naphthyl ring were synthesized according to the methods in Section I. The chemical structures and photochromic performances are summarized in the following Table 3 (compounds 19-24). As shown in Table 3, the presence of an electron withdrawing —CF3 substituent on the naphthyl ring leads to very fast fading kinetics, with t1/2 values as low as 13s.

TABLE 3

| Dye | 19 | 20 | 21 |
|---|---|---|---|
| Structure | (structure) | (structure) | (structure) |
| Color | purple | purple | purple |
| $t_{1/2}$ (s) | 14 | 14 | 13 |
| Dye | 22 | 23 | 24 |

TABLE 3-continued

| Structure | | | |
|---|---|---|---|
| Color | purple | purple | blue |
| $t_{1/2}$ (s) | 14 | 14 | 14 |

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed:

1. A compound comprising the formula G

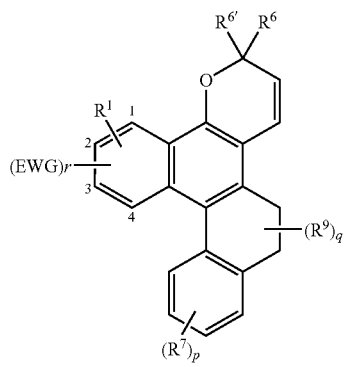

wherein
R$^1$ comprises hydrogen, a linear or branched alkyl group, a cycloalkyl group, a linear or branched alkoxy group, an aryl or heteroaryl group, or an aralkyl or heteroaralkyl group;

EWG comprises an electron-withdrawing group comprising —C(O)R$^5$ at C2 or C3, wherein R$^5$ comprises a straight or branched alkyl group or aryl group;

p is from one to four;
q is one or two;
r is from one to three;

each R$^6$, R$^{6'}$ and R$^7$ comprises, independently, a linear or branched alkyl group, a cycloalkyl group, a linear or branched alkoxy group, a haloalkyl group, a halocycloalkyl group, a haloalkoxy group, an aryl or heteroaryl group, an aralkyl or heteroaralkyl group, or a substituted or unsubstituted phenoxy or naphthoxy group; and each R$^9$ comprises, independently, hydrogen, a hydroxyl group, an alkyl group, an aryl group, or an alkoxy group, wherein when two adjacent R$^9$ groups are present, they may form at least one aromatic or non-aromatic cyclic group, optionally substituted with at least one linear or branched alkyl group, a cycloalkyl group, a linear or branched alkoxy group, an aryl or heteroaryl group, or an aralkyl or heteroaralkyl group.

2. The compound of claim 1, wherein R$^1$ is hydrogen or an alkoxy group.

3. The compound of claim 1, wherein p is one, and R$^7$ is hydrogen or an alkoxy group.

4. The compound of claim 1, wherein q is one, and R$^9$ is hydrogen.

5. The compound of claim 1, wherein R$^1$ is hydrogen or an alkoxy group, p is one, R$^7$ is hydrogen or an alkoxy group, q is one, R$^9$ is hydrogen, and each R$^6$ comprises, independently, an aryl or heteroaryl group.

6. The compound of claim 1, wherein the compound forms a portion of an article.

* * * * *